(12) United States Patent
Benedik

(10) Patent No.: US 7,997,146 B2
(45) Date of Patent: Aug. 16, 2011

(54) DEVICE FOR DETERMINING THE QUALITY AND SOLIDNESS OF THE VASCULAR WALL

(76) Inventor: Jaroslav Benedik, Brno (CZ)

( * ) Notice: Subject to any disclaimer, the term of this patent is extended or adjusted under 35 U.S.C. 154(b) by 357 days.

(21) Appl. No.: 12/358,849

(22) Filed: Jan. 23, 2009

(65) Prior Publication Data

US 2009/0191615 A1    Jul. 30, 2009

(30) Foreign Application Priority Data

Jan. 25, 2008 (CZ) ................................ 2008-19621

(51) Int. Cl.
*G01N 3/08* (2006.01)
*G01N 3/22* (2006.01)

(52) U.S. Cl. ................................ 73/788; 73/826; 73/831

(58) Field of Classification Search ............... 73/54.37, 73/54.39, 150 A, 788, 826, 827, 830, 831, 73/837, 855, 860
See application file for complete search history.

(56) References Cited

U.S. PATENT DOCUMENTS

| 3,926,037 | A | * | 12/1975 | Kopito et al. | ............... | 73/54.37 |
| 4,095,461 | A | * | 6/1978 | Starita | ............... | 73/815 |
| 4,343,190 | A | * | 8/1982 | Danko et al. | ............... | 73/846 |
| 6,285,895 | B1 | * | 9/2001 | Ristolainen et al. | .......... | 600/323 |
| 6,571,610 | B1 | * | 6/2003 | Raffer | .......... | 73/54.35 |
| 6,721,667 | B2 | * | 4/2004 | Banes et al. | ............... | 702/41 |
| 6,833,924 | B2 | * | 12/2004 | Love et al. | ............... | 356/614 |
| 7,249,523 | B2 | * | 7/2007 | Nickerson | .......... | 73/846 |
| 2008/0114283 | A1 | * | 5/2008 | Mattson et al. | ................ | 604/20 |
| 2009/0056424 | A1 | * | 3/2009 | Cohen et al. | ................ | 73/54.37 |
| 2009/0062642 | A1 | * | 3/2009 | Hauck | .......... | 600/429 |

FOREIGN PATENT DOCUMENTS

CZ    292284 B6    8/2008
WO    2007/117782 A1    10/2007

* cited by examiner

*Primary Examiner* — Lisa Caputo
*Assistant Examiner* — Punam Roy
(74) *Attorney, Agent, or Firm* — Hovey Williams LLP

(57) ABSTRACT

A device for determining the quality and solidness of the vascular wall is provided for testing tissue samples and includes opposed first and second fixation plates. The fixation plates are connectable to an air pump or other source of vacuum for fixing the tissue sample in position. The device is connectable to a detector such as a meter, gauge, or printing device capable of displaying or producing an image or display corresponding to the value of a force required to disrupt or break the internal links between individual layers of the vascular wall. The fixation plates are movable relative to one another and may be abducted by abductors connecting the plates or by rotational movement of one fixation plate relative to the other by a shaft or other rotational mechanism.

10 Claims, 3 Drawing Sheets

DEVICE FOR DETERMINING THE QUALITY AND SOLIDNESS OF THE VASCULAR WALL

BACKGROUND OF THE INVENTION

1. Field of the Invention

The technical solution of the present invention concerns a device to determine the quality and solidness of the vascular wall. The device of the present invention involves the field of devices used during surgical procedures and in research of human tissue or tissue of a different organism.

2. Description of the Prior Art

The principle of determining the quality of arterial tissue is currently determined by imperfect technical solutions. The solution described in published International Application WO 2007/117782 deals with determining the quality of tissue and use of various sources for the treatment of this tissue. According to this reference, the probe detects changes in tissue with the introduction of various types of radiation to this tissue, and subsequently examines changes of radiation during passage of the radiation through this tissue. The disadvantage of the described solution of this reference lies in the fact that it does not directly test the quality (solidness) of tissue and therefore does not define the properties and quality of the tissue.

A further known technical solution for examining the tissue of living organisms is described in Czech patent No. 292284. However, the described equipment examines a different nature of the tissue, i.e. its viscosity, and therefore does not address the properties of the tissue with regard to the risk of dissection of the vascular wall.

SUMMARY OF THE INVENTION

One core feature of the proposed technical solution presented by the present invention is a device for determining the quality and solidness of the vascular wall in a destructive way. The device of the present invention is designed to be connected to an air pump or other suction device giving rise to negative pressure on the surface of fixation plates and thus in the space between the fixation plates. A sample of the vascular wall measuring several $mm^2$ to several tens of $mm^2$ inserted in the space between the fixation plates is fixed with the aid of negative pressure by suction to their surface. The layout of moving fixation plates enables the stretching of the tested sample of the vascular wall by mutual movement of the fixation plates up to the point where the internal links are broken between individual layers of the vascular wall. The force required for this disruption is measured and recorded by a detector.

The advantage of the proposed solution is that it is possible to comprehensively decide from the information ascertained about whether preventive cardio-surgery is appropriate or instead to extend the use of an existing surgical procedure. Unlike the known solutions the proposed device need not be used in a strictly sterile environment because the tissue is examined outside the patient's body and the used tissue is not returned to the body.

The device of the present invention provides an important benefit in that enables the user to ascertain current values concerning the quality of the vascular wall of a certain patient or tissue undergoing testing with the possibility of making a comparison of the current values with standard values and to make an informed decision as to whether the current surgical procedure will prove beneficial or is unnecessary.

BRIEF DESCRIPTION OF DRAWINGS

The exemplary version of the proposed solution is described with reference to the drawings wherein.

DESCRIPTION OF THE PREFERRED EMBODIMENTS

EXAMPLE 1

Figure 1:
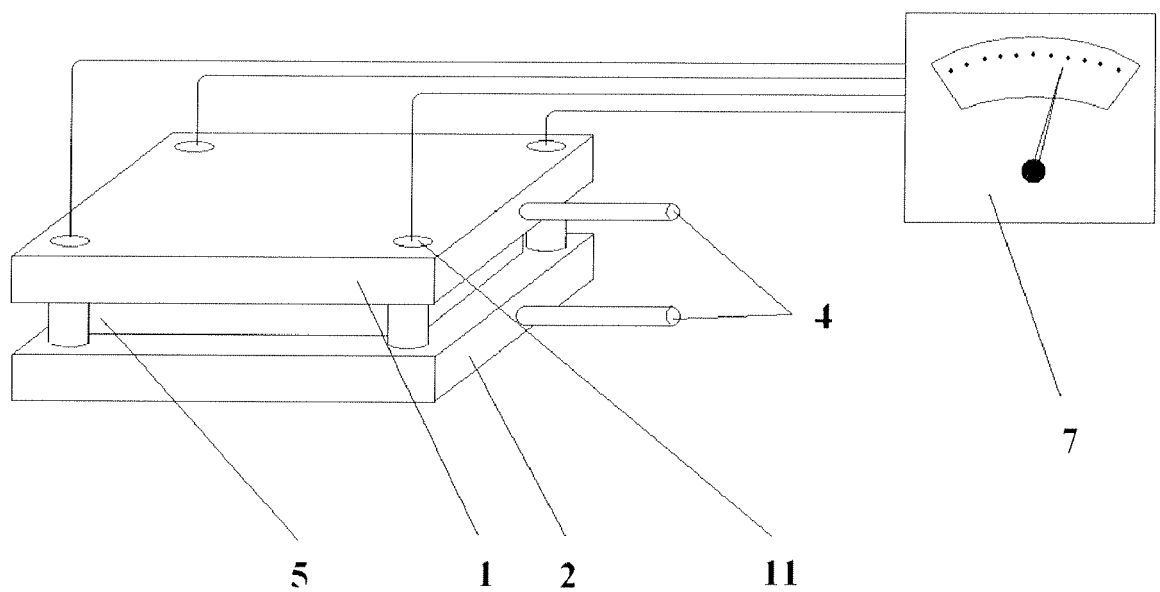
FIG. 1 is an oblique view of the device with linearly abducting square fixation plates and electrical conduits connecting to the detector, with an indicator of the detector indicating a connection to the detector.
Figure 2:
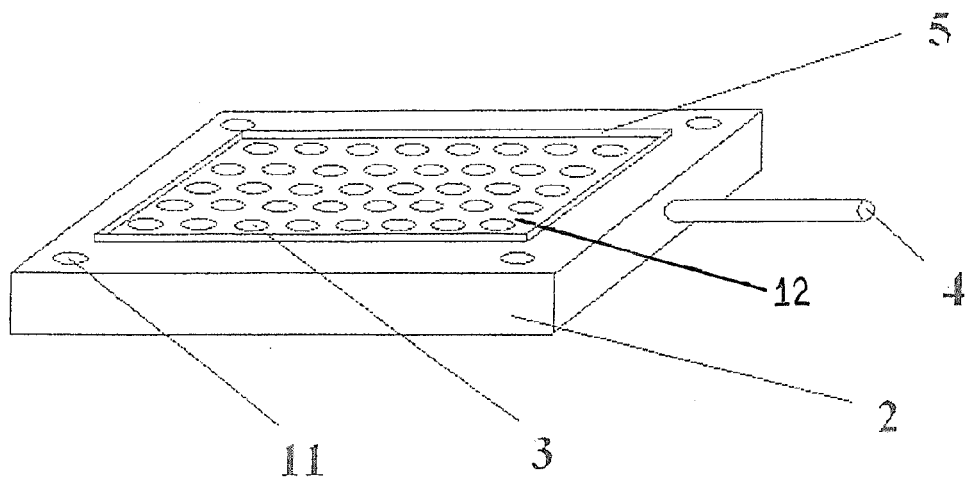
FIG. 2 is an oblique view of the bottom fixation plate as shown in FIG. 1 revealing the arrangement of a blade and holes.
Figure 3:
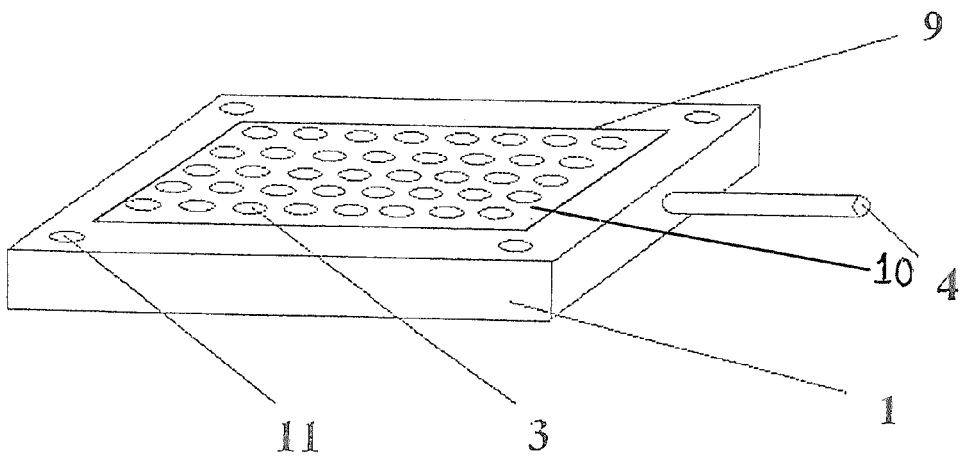
FIG. 3 is an oblique view similar to FIG. 2 showing the top fixation plate in an inverted orientation revealing the arrangement of a groove adapted to receive the blade of the bottom plate of FIG. 2 and the holes.
Figure 4:
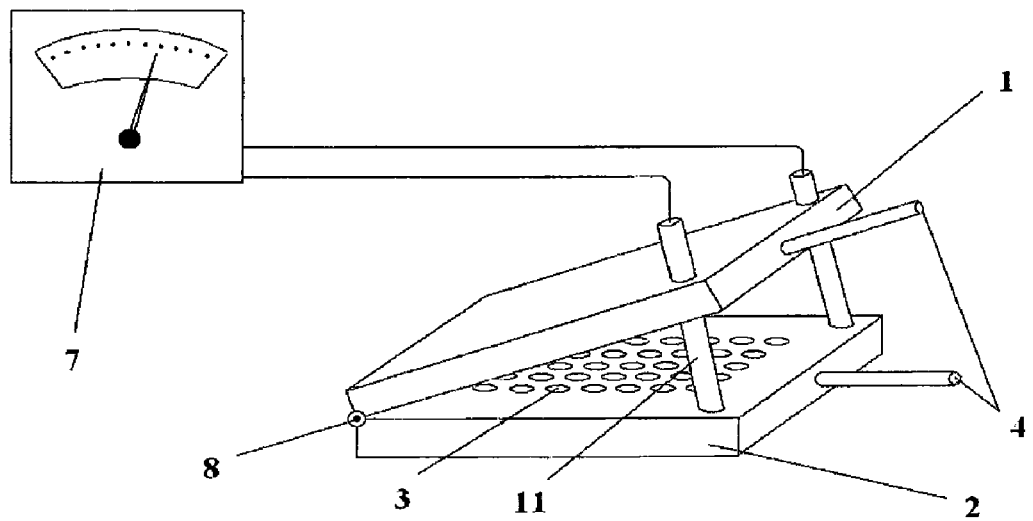
FIG. 4 is an oblique view of the device similar to FIG. 1 with the top fixation plate folded back at an angular orientation to the bottom fixation plate and an indicator of the detector indicating the connection to the detector.

A device has been constructed for testing the quality of the vascular wall according to the proposed solution. The device consists of two fixation plates 1 and 2. The bottom fixation plate 2 is equipped with a square-shaped blade 5, while the top fixation plate 1 is equipped with a groove 9 corresponding in shape and size with blade 5. Both fixation plates 1 and 2 are hollow inside with a set of channels for the equal distribution of negative pressure directed into holes 3. Holes 3 are oriented toward and directed into the space between the fixation plates 1 and 2 and are situated in the areas interior to and defined by the blade 5 and groove 9. These holes 3 allow under-negative pressure to be passed from the outlets 4 (which are operatively connected to an air pump or other fluid suction device, not shown) to the surface of the fixation plates 1 and 2, and thereby make sure a tissue sample, such as a tissue sample of the aortic wall, is fixed. The device also consists of an abductor 11 enabling the abduction of the fixation plates 1 and 2. In this case the fixation plates are abducted linearly and the abductor 11 for abducting the fixation plates 1 and 2 is designed and equipped in this example with four screws which are threaded into receivers (not shown) whereby rotation of the screws extends one of the fixation plates relative to the other. The abductors may also be hydraulic or pneumatic rams, include telescoping rods, or any other device which moves one of the fixation plates away from the other. The force required for abducting the fixation plates 1 and 2 is measured and recorded by detector 7 which is connected to the abductor 11 enabling the abduction of the fixation plates 1 and 2. The described version can be seen in figures no. 1, 2 and 3.

EXAMPLE 2

A device has been constructed for testing the quality of the vascular wall according to the proposed solution. The device consists of two fixation plates 1 and 2 connected with the aid of a hinge or longitudinal joint 8. The fixation plates 1 and 2 are preferably rectangular or square shaped, and for example may be provided with a 20 mm side. Both fixation plates 1 and 2 are hollow inside and include respective top fixation plate wall 10 and bottom fixation plate wall 12 each having a set of holes 3 which are directed into the space between them whereby the outlets are in fluidic communication with the holes. These holes 3 allow negative pressure to be fed from outlets 4 on the surface of fixing plates 1 and 2, and thereby ensuring fixation of a sample. The device also consists of an abductor 11 enabling the abduction of the fixation plates 1 and 2. This abduction can be performed smoothly as well as in steps with defined time delays. The force required to abduct the fixation plates 1 and 2 is measured and recorded by a detector 7 which is connected to the abductor 11 enabling abduction of the fixation plates 1 and 2. The described version can be seen in figure no. 4.

EXAMPLE 3

In use, a tissue sample, preferably of the vascular wall, is taken from a human or veterinary patient, or from a previously collected tissue sample, and placed between the first and second fixation plates 1 and 2. Preferably, the tissue sample corresponds in size and shape to the configuration of the blade 5 extending from the wall of one of the plates and the corresponding groove on the other of the plates and thus is of a standard size. Once positioned, the fixation plates 1 and 2 are brought together and a vacuum air pump or other source of vacuum, which is connected to the outlets 4, is actuated to place the space between the fixation plates under negative pressure. The abductors 11 are electrically connected to detector 7 to provide a signal corresponding to the force required to abduct the fixation plates to abduct the layers of tissue. The measured force corresponds to the force required to stretch and ultimately disrupt the internal links between individual layers of the tissue sample. The force is thus measured and recorded by the detector whereby it may be perceived by the surgeon or others.

INDUSTRIAL APPLICABILITY

The proposed solution can be practically utilized in cardio-surgical operating theatres for all surgical procedures where, based on the testing of the quality of the aortic wall, any surgical indication during the actual procedure will be extended by a procedure carried out on the ascending aorta. The patient's tissue is tested by the device hereof, and if the tissue is not strong enough, the operation is extended to remove the weak tissue of the ascending aorta and substitute stronger tissue.

LIST OF REFERENCE MARKS

1—top fixation plate
2—bottom fixation plate
3—holes
4—outlet
5—blade
7—detector
8—longitudinal joint
9—groove
10—top fixation plate wall
11—abductor
12—bottom fixation plate wall

The invention claimed is:

1. A device for determining the quality and solidness of the vascular wall which can be used to determine the mutual cohesiveness of individual layers of the vascular wall by a destructive method on tissue samples comprising:
   first and second fixation plates which are movable one relative to another and configured for receiving and fixing a tissue sample therebetween; and
   a connector for operatively connecting at least one of the fixation plates to a detector for providing a signal for measuring and/or recording a value corresponding to the solidness of the tissue sample with mutual abduction of the fixation plates,
   wherein the first and second fixation plates are each provided with respective opposing walls having holes, each of said first and second fixation plates further including outlets operatively connected to the holes and adapted for connection to a source of negative fluid pressure for fixing the tissue sample to the first and second fixation plates.

2. The device for determining the quality and solidness of the vascular wall according to claim 1, including an abductor for abducting the one of the first and second fixation plates relative to the other in a direction substantially perpendicular to their respective opposing walls.

3. The device for determining the quality and solidness of the vascular wall according to claim 1 including a longitudinal joint connecting the first and second fixation plates and an abductor for abducting one of the first and second fixation plates relative to the other.

4. The device for determining the quality and solidness of the vascular wall according to claim 1, wherein the first and second fixation plates are each provided with respective opposing walls, and wherein the wall of the first fixation plate includes a blade of a closed geometric shape and wherein the wall of the second fixation plate is provided with a groove complementally shaped and sized with the blade, and wherein the blade and groove determine a standard size of a tissue sample having a surface area adapted to the shape and size of the blade and groove which tissue sample is to be tested by the device.

5. A device for determining the quality and solidness of the vascular wall which can be used to determine the mutual cohesiveness of individual layers of the vascular wall by a destructive method comprising:
   first and second mutually flexible opposite fixation plates, one being movable relative to the other of random shape, and adapted to receive a tissue sample between and fixed to them, the device being connected to a detector for measuring and recording a value corresponding to the solidness of the tissue sample with mutual abduction of the fixation plates;
   wherein the first and second fixation plates are each provided with respective opposing walls having holes, each of said first and second fixation plates further including outlets operatively connected to the holes and adapted for connection to a source of negative fluid pressure for fixing the tissue sample to the first and second fixation plates.

6. The device for determining the quality and solidness of the vascular wall according to claim 5, wherein the fixation plates are capable of being abducted from each other linearly with the aid of an abductor.

7. The device for determining the quality and solidness of the vascular wall according to claim 5, wherein the fixation plates are connected by a longitudinal joint for determining their angular abduction with the aid of an abductor.

8. The device for determining the quality and solidness of the vascular wall according to claim 5, wherein each of the first and second fixation plates include a wall, said wall of the first fixation plate being opposite to the wall of the second fixation plate, and wherein the opposite walls of the fixation plates are equipped with a blade of a closed geometric shape in one of the walls and a groove in the other of the walls, said groove having a shape and size corresponding to the blade, for determining a standard size of a tissue sample to be tested, the tissue sample having a surface area which is adapted to the shape of the blade and groove.

9. A device according to claim 5, wherein said first and second fixation plates are connected to one another by a hinge and are adapted to be shifted away from each other by pivoting about said hinge by an opening element.

10. A device according to claim 5, wherein the wall of said first fixation plate is provided with a blade of a closed geometric shape and the wall of the second fixation plate is provided with a complementally shaped groove, the blade and the groove determining a standard size of the tissue sample, and wherein the openings are located in the areas of the wall defined within the blade and the groove of the respective first and second fixation plates.

* * * * *